United States Patent [19]

Nakajima et al.

[11] Patent Number: 5,571,683

[45] Date of Patent: Nov. 5, 1996

[54] β-GLUCANS DETECTION REAGENTS AND METHODS OF DETECTING β-GLUCANS

[75] Inventors: Hiroshi Nakajima; Hisashi Yamamoto; Junko Cho, all of Tukuba, Japan

[73] Assignee: Maruha Corporation, Japan

[21] Appl. No.: 322,171

[22] Filed: Oct. 12, 1994

Related U.S. Application Data

[63] Continuation of Ser. No. 953,922, Sep. 29, 1992, abandoned.

[30] Foreign Application Priority Data

Dec. 25, 1991 [JP] Japan ................. 3-343617

[51] Int. Cl.$^6$ ............... C12Q 1/54; C12Q 1/00; C12Q 1/37; C12N 1/14
[52] U.S. Cl. ................. 435/14; 435/4; 435/24; 435/23; 435/29; 435/34; 435/18; 435/13; 435/254.1; 435/963; 436/63
[58] Field of Search ................. 435/14, 29, 23, 435/4, 34, 13, 18, 24, 254.1, 963; 436/63

[56] References Cited

U.S. PATENT DOCUMENTS

| | | | |
|---|---|---|---|
| 4,188,264 | 2/1980 | Iwanaga et al. | 435/23 |
| 4,322,217 | 3/1982 | Dikeman | 435/23 |
| 4,495,294 | 1/1985 | Nakahara et al. | 435/23 |
| 4,510,241 | 4/1985 | Mills | 435/23 |
| 4,663,298 | 5/1987 | Urbascheck et al. | 435/23 |
| 5,068,314 | 11/1991 | Nakamura | 530/317 |
| 5,310,657 | 5/1994 | Berzofsky | 435/34 |

FOREIGN PATENT DOCUMENTS

| | | |
|---|---|---|
| 0491047 | 6/1992 | European Pat. Off. |
| 2-053799 | 2/1990 | Japan . |
| 2-152987 | 6/1990 | Japan . |
| 2-138193 | 8/1990 | Japan . |
| 2204500 | 8/1990 | Japan . |
| 2-207098 | 8/1990 | Japan . |
| 2-270897 | 11/1990 | Japan . |
| WO9109052A | 6/1991 | WIPO . |

OTHER PUBLICATIONS

Chemical Abstracts vol. 97(3): 19652 p (1981).
Takezawa, J. (1991) Plasma Level of Θ-glucan for Diagnosis and Treatment of Candida SepsisJ. Oshaka Univ. School of Medicine 41:133–142.
Miyata, et al. (1989) Antimicrobial Peptides Isolated From Horseshoe Crab Hemocytes, Tachyplesin II, and Polyphemusins I and II: Chemical Structures and Biological Activity J. Biochem 106:663–668.

*Primary Examiner*—John Kight
*Assistant Examiner*—Louise N. Leary
*Attorney, Agent, or Firm*—Limbach & Limbach, L.L.P.

[57] ABSTRACT

A β-glucan detection reagent includes a horseshoe crab hemocyte lysate containing an endotoxin neutralizing peptide and a chromogenic substrate. The reagent provides a very sensitive method for detecting β-glucans and is therefore useful as a diagnostic agent such as for detection of nosomycosis.

13 Claims, 1 Drawing Sheet

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 3
        ( B ) TYPE:amino acid
        ( C ) STRANDEDNESS:
        ( D ) TOPOLOGY:Linear ( i i ) MOLECULE TYPE:peptide ( v i ) ORIGINAL SOURCE:
        ( A ) ORGANISM:
        ( B ) CELL TYPE:
        ( C ) CELL LINE:

( i x ) FEATURE:
        ( A ) LOCATION:1
        ( B ) NAME/KEY: Xaa =Boc-Leu where Boc represents
            tert- butyloxycarbonyl
        ( A ) LOCATION:3
        ( B ) NAME/KEY: Xaa =Arg-pNa where pNa represents
            para- nitroaniline ( x i ) SEQUENCE DESCRIPTION:SEQ ID NO:1:

Xaa  Gly  Xaa ( 2 ) INFORMATION FOR SEQ ID NO:2:

( i ) SEQUENCE CHARACTERISTICS:
        ( A ) LENGTH: 3
        ( B ) TYPE:amino acid
        ( C ) STRANDEDNESS:
        ( D ) TOPOLOGY:Linear ( i i ) MOLECULE TYPE:peptide ( v i ) ORIGINAL SOURCE:
        ( A ) ORGANISM:
        ( B ) CELL TYPE:
        ( C ) CELL LINE:

( i x ) FEATURE:
        ( A ) LOCATION:1
        ( B ) NAME/KEY: Xaa =Boc-Leu where Boc represents
            tert- butyloxycarbonyl -continued (A) LOCATION:3
        (B) NAME/KEY: Xaa =Arg-McA where McA represents
            methylcoumarin (xi) SEQUENCE DESCRIPTION:SEQ ID NO:2:

Xaa Gly Xaa (2) INFORMATION FOR SEQ ID NO:3:

(i) SEQUENCE CHARACTERISTICS:
        (A) LENGTH: 4
        (B) TYPE:amino acid
        (C) STRANDEDNESS:
        (D) TOPOLOGY:Linear (ii) MOLECULE TYPE:peptide (vi) ORIGINAL SOURCE:
        (A) ORGANISM:
        (B) CELL TYPE:
        (C) CELL LINE:

(ix) FEATURE:
        (A) LOCATION:1
        (B) NAME/KEY: Xaa =Boc-Ile where Boc represents
            tert- butyloxycarbonyl
        (A) LOCATION:4
        (B) NAME/KEY: Xaa =Arg-pNa where pNa represents
            para- nitroaniline (xi) SEQUENCE DESCRIPTION:SEQ ID NO:3:

Xaa Glu Gly Xaa (2) INFORMATION FOR SEQ ID NO:4:

(i) SEQUENCE CHARACTERISTICS:
        (A) LENGTH: 4
        (B) TYPE:amino acid
        (C) STRANDEDNESS:
        (D) TOPOLOGY:Linear (ii) MOLECULE TYPE:peptide (vi) ORIGINAL SOURCE:
        (A) ORGANISM:
        (B) CELL TYPE:
        (C) CELL LINE:

(ix) FEATURE:
        (A) LOCATION:1
        (B) NAME/KEY: Xaa =Boc-Val where Boc represents
            tert- butyloxycarbonyl
        (A) LOCATION:4
        (B) NAME/KEY: Xaa =Arg-pNa where pNa represents
            para- nitroaniline (xi) SEQUENCE DESCRIPTION:SEQ ID NO:4:

Xaa Leu Gly Xaa (2) INFORMATION FOR SEQ ID NO:5:

(i) SEQUENCE CHARACTERISTICS:
        (A) LENGTH: 4
        (B) TYPE:amino acid
        (C) STRANDEDNESS:
        (D) TOPOLOGY:Linear (ii) MOLECULE TYPE:peptide (vi) ORIGINAL SOURCE:
        (A) ORGANISM:
        (B) CELL TYPE:
        (C) CELL LINE:

( i x ) FEATURE:
  ( A ) LOCATION:1
  ( B ) NAME/KEY: Xaa =Bz-Ile where Bz represents benzyl
  ( A ) LOCATION:4
  ( B ) NAME/KEY: Xaa =Arg-pNa where pNa represents para- nitroaniline ( x i ) SEQUENCE DESCRIPTION:SEQ ID NO:5:

Xaa Glu Gly Xaa

β-GLUCANS DETECTION REAGENTS AND METHODS OF DETECTING β-GLUCANS

This is a continuation of application Ser. No. 07/953,922 filed on Sep. 29, 1992 now abandoned, and claims to priority under 35 U.S.C. §120 to Japanese patent application Ser. No. 343617/1991 filed on Dec. 25, 1991.

BACKGROUND OF THE INVENTION

The present invention relates to β-glucans detection reagents which are used as diagnostic agents for nosomycosis in the pharmaceutical field and to methods of detecting β-glucans using the reagents.

Currently, it has been attempted to detect nosomycosis at an early stage by determining the concentration of β-glucans in blood because fungi contain β-glucans in their components (Journal issued by Ohsaka University, School of Medicine, 41 (3): 133–142). Reagents specific to β-glucans are therefore useful to detect nosomycosis and can be used as diagnostic agents in the pharmaceutical field.

It is known that the β-glucans coagulate hemocyte lysate of horseshoe crabs, the finding that can be utilized to quantitatively determine levels of β-glucans in blood. However, endotoxins also coagulate the hemocyte lysate of the horseshoe crabs. This is because the hemocyte lysate of the horseshoe crabs contain both an activator of the precursor of a β-glucan coagulatory enzyme and an activator of the precursor of an endotoxin coagulatory enzyme.

The present inventors have successfully made reagents that specifically reacts with β-glucans alone by removing or inactivating an activator of the precursor of an endotoxin coagulatory enzyme in the hemocyte lysate of a horseshoe crab, and filed this invention (Japanese Patent Application KOKAI Nos. 138193/1990, 207098/1990).

The invention disclosed in Japanese Patent Application KOKAI No. 138193/1990 relates to the hemocyte lysate specific to β-glucans obtained by fractionating the hemocyte lysate by ion exchange chromatography using sulfopropyl as an adsorbent.

The invention disclosed in Japanese Patent Application KOKAI No. 207098/1990 relates to the hemocyte lysate specific to β-glucans which comprises an endotoxin neutralizing peptide plus a limulus reagent used in the typical gelation procedure.

The present invention relates to the hemocyte lysate specific to β-glucans obtained by extracting the hemocytes of American horseshoe crabs with 20 mM Tris-HCl buffer/pH 8.0 containing 12 mM $MgCl_2$ and adding polyphemusin to the hemocyte lysate. The polyphemusin is obtained by extracting the precipitate of the hemocyte lysate with 20 mM HCl and purifying the resultant extract by reverse phase HPLC.

The hemocyte lysate specific to β-glucans can detect as little as 0.1 ng/ml of carboxymethyl curdlan but does not react with as little as 100 ng/ml of the Nippon Pharmacopoeia standard endotoxin.

The method of the invention disclosed in Japanese Patent Application KOKAI No. 138193 is required to perform chromatography on endotoxin-free samples, which makes reagent preparing procedures complicated. In addition, although the method of preparing reagents disclosed in Japanese Patent Application KOKAI No. 138193/1990 is easy, a limulus reagent itself used in the gelation procedure is not suitable for quantitative analysis and its sensitivity is as low as 0.1 ng/ml.

It is an object of the present invention to provide a β-glucans detection reagent which is easily prepared and very sensitive and a method of detecting β-glucans using the reagent.

The present inventors have studied a reagent to detect β-glucans, a reagent which is easily prepared and very sensitive, and found an easy method of preparing a β-glucans detection reagent by combining typical endotoxin detection reagents with endotoxin neutralizing peptides derived from horseshoe crab hemocytes and chromogenic substrates.

SUMMARY OF THE INVENTION

The present invention relates to a β-glucan detection reagent which comprises horseshoe crab hemocyte lysates containing endotoxin neutralizing peptides derived from horseshoe crab hemocytes and chromogenic substrates. The present invention also relates to a method of detecting β-glucans using the β-glucan detection reagent described above.

The β-glucan detection reagent of the invention is easily prepared, very sensitive, and useful for medical fields as a diagnostic agent for fungus diseases.

DETAILED DESCRIPTION OF THE INVENTION

Figure 1:
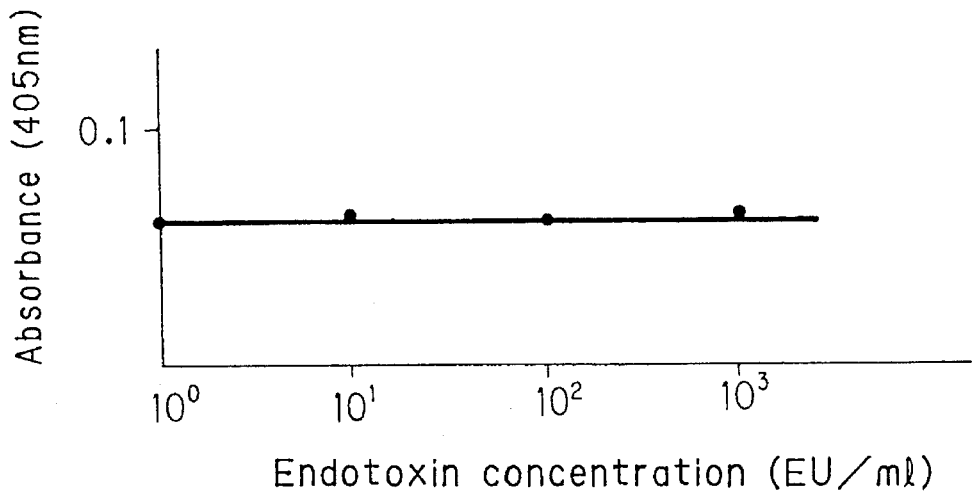
FIG. 1 shows sensitivity of the β-glucans detection reagent of the invention to endotoxin.

Suitable horseshoe crabs for the horseshoe crab lysate of the invention include *Tachypleus tridentatus, Tachypleus gigas, Limulus polyphemus* and the like.

The invention utilizes any endotoxin neutralizing peptides derived from horseshoe crabs, such as Tachyplesin-I, Tachyplesin-II, Tachyplesin-III, Polyphemusin-I, or Polyphemusin-II. These peptides are described in detail in the Japanese Patent Application KOKAI Nos. 53799/1990 (Polyphemusin-I), 152987/1990 (Polyphemusin-II), 270897/1990 (Tachyplesin-III), or U.S. Pat. No. 5,068,314 to Nakamura, et al. (Tachyplesin-I), or J. Biochem. 106: 663–668, 1989 (Tachyplesin-II). One of the methods of preparing these peptides is briefly described as follows.

Polyphemusin I

Tris-HCl buffer containing sodium chloride and benzamidine hydrochloride is added to the hemocyte of the North American horseshoe crab (*Limulus polyphemus*). The hemocyte is disrupted and then centrifuged. An HCl solution is added to the precipitate, which is disrupted and centrifuged. The supernatant is loaded onto a Sephadex G-50 column, to which an HCl solution is then added. Fractions at absorbance 280 nm are collected and loaded onto a Cosmosil 5C18 column. A trifluoroacetic acid solution in which the concentration of acetonitril is altered is then added to the column to give polyphemusin I.

Polyphemusin II

Polyphemusin II is also obtained from the North American horseshoe crab by a similar manner as described in Polyphemusin I. Polyphemusin II is separated by the difference in elution time.

Tachyplesin-I and Tachyplesin-II

These are obtained from Asian horseshoe crabs (*Tachypleus tridentatus, Tachypleus gigas*) by a similar manner as described in polyphemusin I and II: the insoluble fractions of Asian horseshoe crab extracts are extracted with an HCl solution and the extract is purified by a Sephadex G-50 column and reverse phase HPLC.

Tachyplesin-III

Tachyplesin-III is obtained from the Malaysian horseshoe crab (*Tachypleus gigas*) by a similar manner as described in polyphemusin I.

An alternative to the method described above, these peptides can be obtained by a solid-phase procedure. When the solid-phase procedure is used, an α-amino group of any amino acids should be protected by a tert-butyloxycarbonyl group (Boc group), and a group attached to an amino acid is preferably protected by converting the amino acid as follows:

Arginine is converted to tosylarginine to protect the guanidino group;

Lysine is converted to 2-chlorobenzyloxycarbonyllysine to protect the ε-amino group;

Cysteine is converted to 4-methylbenzylcysteine to protect the thiol group;

Tyrosine is converted to benzyltyrosine to protect the hydroxyl group; and

Tryptophan is converted to formyltryptophan to protect the indole ring.

Protected form Arginine (Arginine derivative), a C-terminal amino acid, is introduced into a phenylacetamidomethyl resin and a polypeptide chain is extended one by one to give rise a protected peptide resin. The protected peptide resin thus synthesized is treated with hydrogen fluoride to separate the protected peptide from the resin. Concurrently, the protected peptide is deprotected, and reduced to give a synthetic peptide by the method known in the art. The crude synthetic peptide thus obtained is purified by the method known in the art such as gel-filtration, reverse phase HPLC and the like. The solid-phase procedure employed to synthesize the peptide is carried out according to the method described in Biochemistry Experiment (I), Nippon Biochemistry Meeting ed., Protein Chemistry, 4: 208–495, Tokyo Kagaku Dojin Press (1977); "Merrifield et al method" in Peptide synthesis by Izumiya, N., Maruzen K. K. Press (1975).

Chemical structures of these peptides are shown below.

Tachyplesin-I

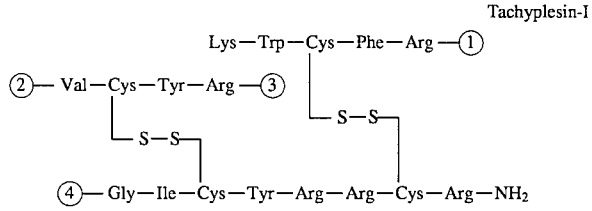

Tachyplesin-II

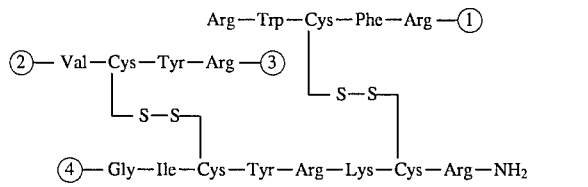

Tachyplesin-III

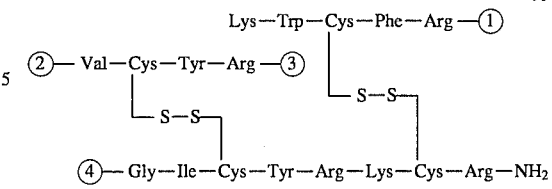

Polyphemusin-I

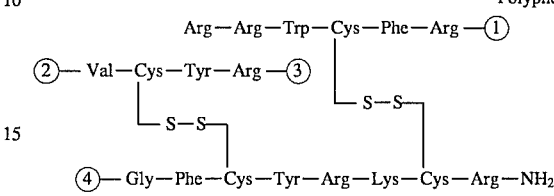

Polyphemusin-II

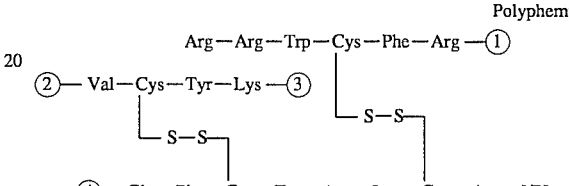

(wherein a pair of 1 and 2, or a pair of 3 and 4 each is directly linked and Arg-$NH_2$ means that a carboxyl group of arginine is amide).

Chromogenic substrates in the present invention include Boc-Leu-Gly-Arg-pNa, Boc-Leu-Gly-Arg-McA, Boc-Ile-Glu-Gly-Arg-pNa, Boc-Val-Leu-Gly-Arg-pNa, Bz-Ile-Glu-Gly-Arg-pNa (wherein pNa represents p-nitroaniline and McA represents methylcoumarin).

An amount of endotoxins neutralizing peptides in the β-glucans detection reagent of the present invention is preferably 0.5–2 mg per a 20-tests vial 0.025–0.1 mg per measurement.

Concentration of β-glucans in samples can be determined as follows. A chromogenic substrate, for example, Boc-Leu-Gly-Arg-pNa, is used, and the β-glucans detection reagent is added to a sample. The reaction mixture is incubated at 37° C. for 30 minutes. After incubation, 0.4N acetic acid is added to the reaction mixture to terminate the reaction. The reaction product is measured for absorbance (at 405 nm) and concentration of β-glucan in the sample is determined by referring to the calibration curve made of known concentrations of β-glucans.

The present invention will be further described by Examples, which are not intended to limit the scope of the present invention.

Examples

1. Preparation of Hemocyte Lysates of Horseshoe Crabs 100 ml of 20 mM Tris-HCl/pH 7.2 containing 150 mM sodium chloride was added to 10 g of hemocytes of the Chinese *Tachypleus tridentatus*. The hemocytes were disrupted and centrifuged at 3,500 rpm for 30 minutes. The resulting supernatant was used as a hemocyte lysate of horseshoe crabs.

2. Preparation of endotoxin neutralizing peptide (Tachyplesin-III)

500 ml of 20 mM Tris-HCl/pH 7.2 containing 50 mM sodium chloride and 2 mM benzamidine hydrochloride was added to 50 g of hemocytes of Malaysian *Tachypleus gigas*. The hemocytes were disrupted and centrifuged at 3,500 rpm for 30 minutes. 500 ml of a 20 mM hydrochloric acid solution was added to the resulting precipitant. The mixture was then disrupted again and centrifuged. Disruption and centrifugation procedures were repeated three more times and the supernatant was pooled each time. The supernatant was lyophilized. After lyophilization, the lyophilized sample was dissolved in a small amount of a 20 mM hydrochloric acid solution. The mixture was loaded onto a Sephadex G-50 column, to which a 20 mM hydrochloric acid solution was added. The eluant was tested for absorbance at 280 nm. The last half portion after the peak absorbance was collected and lyophilized.

The lyophilized sample was dissolved in a small amount of a 20 mM hydrochloric acid solution. The mixture was loaded onto Cosmosil® 5C18 column. Trifluoroacetic acid solution, in which the concentration of acetonitril was altered, was added to the column to elute Tachyplesin III.

3. Preparation for β-glucan Specific Reagents

Tachyplesin III was dissolved in a 4% mannitol solution to a final concentration of 2 mg/ml. 0.5 ml of the resulting solution was combined with 0.5 ml of a horseshoe crab hemocyte lysate. To the mixture, 0.2 ml of a 5 mM Boc-Leu-Gly-Arg-pNa solution was added. The resulting mixture was lyophilized to give a desired reagent.

4. Sensitivity Test of β-glucan Detection Reagents to β-glucan and Endotoxins

The sensitivity of β-glucan detection reagents of the present invention to endotoxin (Nippon Pharmacopeia Standard Products) and β-glucan was tested as follows.

The β-glucans reagent was dissolved in 2.1 ml of 40 mM Tris-HCl buffer/pH 7.2 and the solution was dispensed, 0.1 ml each, to sterilized tubes. 0.1 ml of increased concentrations of endotoxins and β-glucans was added to the tube. The tube was vortexed and incubated at 37±1° C. for 30±1 minutes. After incubation, 0.4 ml of 0.4N acetic acid was added to the tube to terminate the reaction. Absorbance (at 405 nm) of the reaction product was measured.

Figure 2:
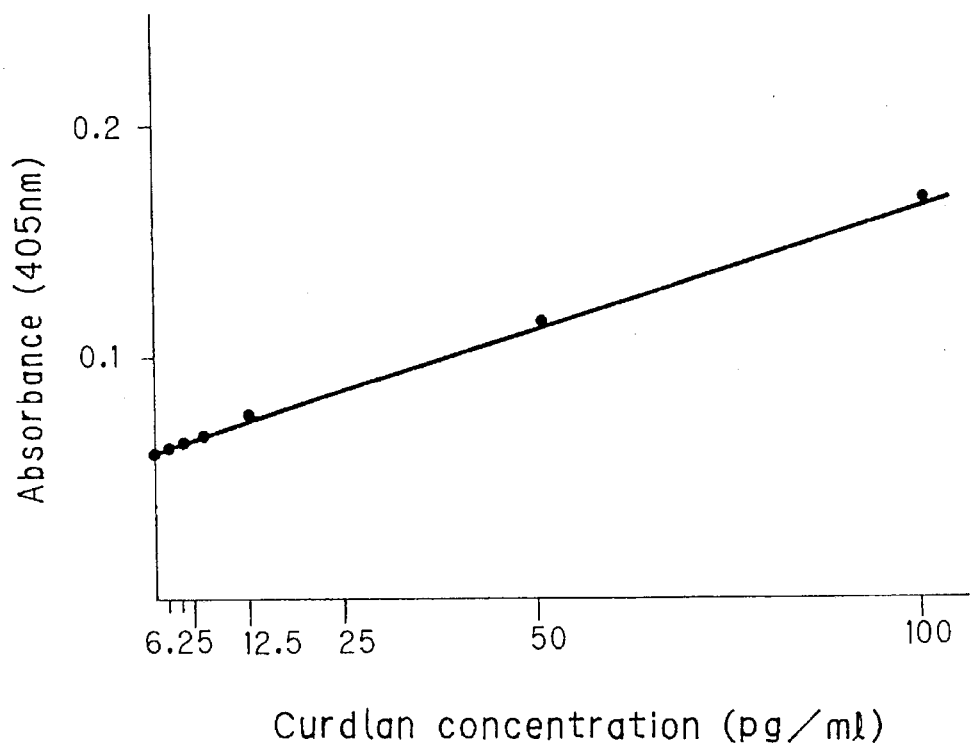
FIG. 2 shows sensitivity of the β-glucans detection reagent of the invention to β-glucans.

FIG. 1 shows a calibration curve of endotoxin. FIG. 2 shows a calibration curve of β-glucan.

---

What is claimed is:

1. A β-glucan detection reagent comprising a horseshoe crab hemocyte lysate containing an endotoxin neutralizing peptide and a chromogenic substrate.

2. The β-glucan detection reagent of claim 1 in which the endotoxin neutralizing peptide derived from horseshoe crab hemocytes comprises Tachyplesin-I, Tachyplesin-II, Tachyplesin-III, Polyphemusin-I, or Polyphemusin-II.

3. The β-glucan detection reagent of claim 1 in which the chromogenic substrate is selected from the group consisting of the peptides of Sequence Identification Numbers 1–5.

4. The β-glucan detection reagent of claim 3 wherein the endotoxin neutralizing peptide is selected from the group consisting of Tachyplesin-I, Tachyplesin-II, Tachyplesin-III, Polyphemusin-I, Polyphemusin-II and combinations thereof.

5. A method for detecting the concentration of β-glucans in a sample comprising adding a reagent comprising a mixture of a horseshoe crab hemocyte lysate, a chromogenic substrate, and an endotoxin neutralizing peptide to the sample;

reacting the sample at 37° C. for 30 minutes;

terminating the reaction by adding an acidic solution to the sample; and measuring the analytically detectable product.

6. The method of claim 5 wherein the endotoxin neutralizing peptide is selected from the group consisting of Tachyplesin-I, Tachyplesin-II, Tachyplesin-III, Polyphemusin-I, Polyphemusin-II and combinations thereof.

7. The method of claim 6 wherein the concentration of endotoxin neutralizing peptide is 0.025–0.1 mg per measurement.

8. The method of claim 5 wherein the chromogenic substrate is selected from the group consisting of the peptides of Sequence Identification Numbers 1–5.

9. The method of claim 5 wherein the analytically detectable product is detected by spectroscopic means.

10. The method of claim 5 wherein said reaction is terminated by the addition of 0.4N acetic acid.

11. The method of claim 5 wherein said measuring step comprises measuring the absorbance of said sample at 405 nm.

12. The method of claim 5 further comprising the step of purifying said peptide by column chromotography prior to adding said reagent to said sample.

13. A composition of matter comprising:

(a) horseshoe crab hemocyte lysate;

(b) an endotoxin neutralizing peptide selected from the group consisting of Tachyplesin-I, Tachyplesin-II, Tachyplesin-III, Polyphemusin-I and Polyphemusin-II; and (c) a chromogenic substrate.

* * * * *